US00PP09303P

United States Patent [19]

VandenBerg

[11] Patent Number: Plant 9,303

[45] Date of Patent: Sep. 26, 1995

[54] CHRYSANTHEMUM PLANT NAMED 'IMPERIAL'

[75] Inventor: Cornelis P. VandenBerg, Salinas, Calif.

[73] Assignee: Yoder Brothers, Inc., Barberton, Ohio

[21] Appl. No.: 280,528

[22] Filed: Jul. 26, 1994

[51] Int. Cl.[6] ..... A01H 5/00

[52] U.S. Cl. ..... Plt./77

[58] Field of Search ..... Plt./76, 77, 78

[56] References Cited

U.S. PATENT DOCUMENTS

Plt. 4,137 10/1977 Kashami ..... Plt./78

Plt. 4,251 5/1978 Iwasaki ..... Plt./77

*Primary Examiner*—Howard J. Locker

*Attorney, Agent, or Firm*—Foley & Lardner

[57] ABSTRACT

A Chrysanthemum plant named Imperial particularly characterized by its flat capitulum form; spooned decorative capitulum type; cream-white ray florets with cream-yellow center of the flower; diameter across face of capitulum of 111 to 140 mm when fully opened, when grown as a pinched disbudded pot mum; photoperiodic flowering response to short days of 51 to 58 days; plant height, with 20 to 26 long days after sticking unrooted cuttings, and with 1 to 2 applications of 2500 ppm B-9 SP, ranges from 20 to 28 cm when grown as a pinched pot mum with four cuttings in a 15 cm pot; branching pattern is spreading and prolific, each plant having 4 to 5 laterals after pinch; and recommended as disbudded pot mum.

3 Drawing Sheets

The present invention comprises a new and distinct cultivar of Chrysanthemum, botanically known as *Dendranthema grandiflora,* and referred to by the cultivar name Imperial.

Imperial, identified as 5490 (90-749001), was originated from a cross made by Cornelis P. VandenBerg in a controlled breeding program in Salinas, Calif., in 1989.

The female parent of Imperial was the cultivar Envy, disclosed in U.S. Plant Pat. No. 5,986, and described as a disbud pot mum with flat capitulum form; decorative capitulum type; ivory and white ray floret color; a diameter across face of capitulum of 100 to 120 mm when grown as a disbudded pot mum; flowering response to short days in Salinas, Calif. of 49 to 54 days; plant height of 20 to 28 cm when grown with 21 to 22 long days after sticking unrooted cuttings prior to start of short days and 2 3 applications of 2500 ppm B-9 SP; and a branching pattern of 3 to 4 laterals developing after pinch.

The male parent of Imperial was an unnamed seedling, identified as 6145 (85-218002), and described as a disbud pot mum with flat capitulum form; spooned decorative capitulum type; yellow ray floret color; diameter across face of capitulum of 114 to 121 mm when grown as a disbudded pot mum; flowering response to short days in Salinas, Calif. of 51 to 55 days; plant height of 20 to 28 cm when grown with 15 to 23 long days after sticking unrooted cuttings prior to start of short days and 1 to 2 applications of 2500 ppm B-9 SP; and a branching pattern of 4 to 5 laterals developing after pinch.

Imperial was discovered and selected as one flowering plant within the progeny of the stated cross by Cornelis P. VandenBerg in Dec. 1990, in a controlled environment in Salinas, Calif.

The first act of asexual reproduction of Imperial was accomplished when vegetative cuttings were taken from the initial selection in Mar. 1991 in a controlled environment in Salinas, Calif., by technicians working under supervision of Cornelis P. VandenBerg.

Horticultural examination of controlled flowerings of successive plantings has shown that the unique combination of characteristics as herein disclosed for Imperial are firmly fixed and are retained through successive generations of asexual reproduction.

Imperial has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Imperial, which, in combination, distinguish this Chrysanthemum as a new and distinct cultivar.

1. Flat capitulum form.
2. Spooned decorative type.
3. Cream-white ray florets with cream-yellow center of the flower.
4. Diameter across face of capitulum of 111 to 140 mm when fully opened, when grown as a pinched disbudded pot mum.
5. Photoperiodic flowering response to short days of 51 to 58 days.
6. Plant height, with 20 to 26 long days after sticking unrooted cuttings, and with 1 to 2 applications of 2500 ppm B-9 SP, ranges from 20 to 28 cm when grown as a pinched pot mum with four cuttings in a 15 cm pot.
7. Branching pattern is spreading and prolific, each plant having 4 to 5 laterals after pinch.
8. Recommended as disbudded pot mum.

The accompanying photographic drawings show typical inflorescence and leaf characteristics of Imperial, with the colors being as nearly true as possible with illustrations of this type.

Sheet 1 is a color photograph of Imperial grown as a pinched disbudded pot mum with four cuttings in a 15 cm pot.

Sheet 2 is a black and white photograph of three views of the inflorescence of Imperial.

Sheet 3 is a black and white photograph showing the upper and under sides of the leaves of Imperial at 3 stages of development (mature, intermediate and immature). In sheets 2 and 3 a measuring tape in centimeters has been added.

Of the commercial cultivars known to the inventor, the most similar in comparison to Imperial is the female parent Envy. Reference is made to attached Chart A, which compares certain characteristics of Imperial to the same characteristics of Envy.

Similar traits are capitulum form, and recommend use as a disbudded pot mum. Imperial has a more cream ray floret color, with more yellow in the center of the flower than Envy, the ray floret color of which is described as white-ivory, with a cream center of the flower. Imperial has a spooned decorative capitulum type, while Envy has a decorative capitulum type. The diameter of capitulum of Imperial is larger, the flowering response is slower, and the branching pattern of Imperial develops one more lateral when compared with Envy. The plant height of Imperial and Envy, not represented in Chart A, is comparable. However, Imperial requires one less growth regulator application to attain a similar plant height as Envy.

In the following description color references are made to The Royal Horticultural Society Colour Chart. The color values were determined on plant material grown as a pinched disbudded pot mum in Salinas, Calif. on Apr. 29, 1994.

Classification

*Botanical.*—*Dendranthema grandiflora* cv Imperial.

*Commercial.*—Spooned decorative disbud pot mum.

Inflorescence

A. Capitulum:

*Form.*—Flat.

*Type.*—Spooned decorative.

*Diameter across face*—111 to 140 mm when fully opened

B. Corolla of ray florets:

*Color (general tonality from a distance of three meters.*—Cream-white with cream-yellow center of the flower.

*Color (upper surface)*.155A. Center of flower closest to 3C (The photograph does not accurately depict the color of flower center which is more golden yellow in the photograph than the actual color value of R.H.S. 3C).

*Color (under surface)*.—155A.

*Shape.*—Longitudinal straight to incurving for the immature ray florets in the center of the flower. Ray florets are tubular with the apex spatulate.

C. Corolla of disc florets:

*Color (mature)*: 144B.

*Color (immature)*: 144A.

D. Reproductive organs:

*Androecium.*—Present on disc florets only; scant pollen.

*Gynoecium.*—Present on both ray and disc florets.

Plant

General appearance:

*Height.*—20 to 28 cm when grown as a pinched pot mum with four cuttings in a 15 cm pot with 20 to 26 long days after direct sticking unrooted cuttings prior to start of short days, and with 1 to 2 applications of 2500 ppm B-9 SP.

*Branching pattern.*—Spreading and prolific, with 4 to 5 laterals after pinch.

Foliage:

*Color (upper surface)*.—147A.

*Color (under surface)*.—147B.

*Shape.*—Lobed and serrated.

CHART A

COMPARISON OF IMPERIAL AND ENVY

| CULTIVAR | IMPERIAL | ENVY |
|---|---|---|
| Ray floret color | Cream-white | White-ivory |
| Center of flower | Cream-yellow | Cream |
| Capitulum form and | Flat | Flat |
| type | Spoon decorative | Decorative |
| Diameter across face of capitulum | 111 to 140 mm | 100 to 120 mm |
| Flowering response | 51 to 58 days | 49 to 54 days |
| Branching pattern | 4 to 5 laterals | 3 to 4 laterals |
| Recommended as | Disbud pot mum | Disbud pot mum |

COMPARISONS MADE OF PLANTS GROWN AS PINCHED DISBUDDED MUMS IN SALINAS, CALIFORNIA

I claim:

1. A new and distinct Chrysanthemum plant named Imperial, as described and illustrated.

* * * * *

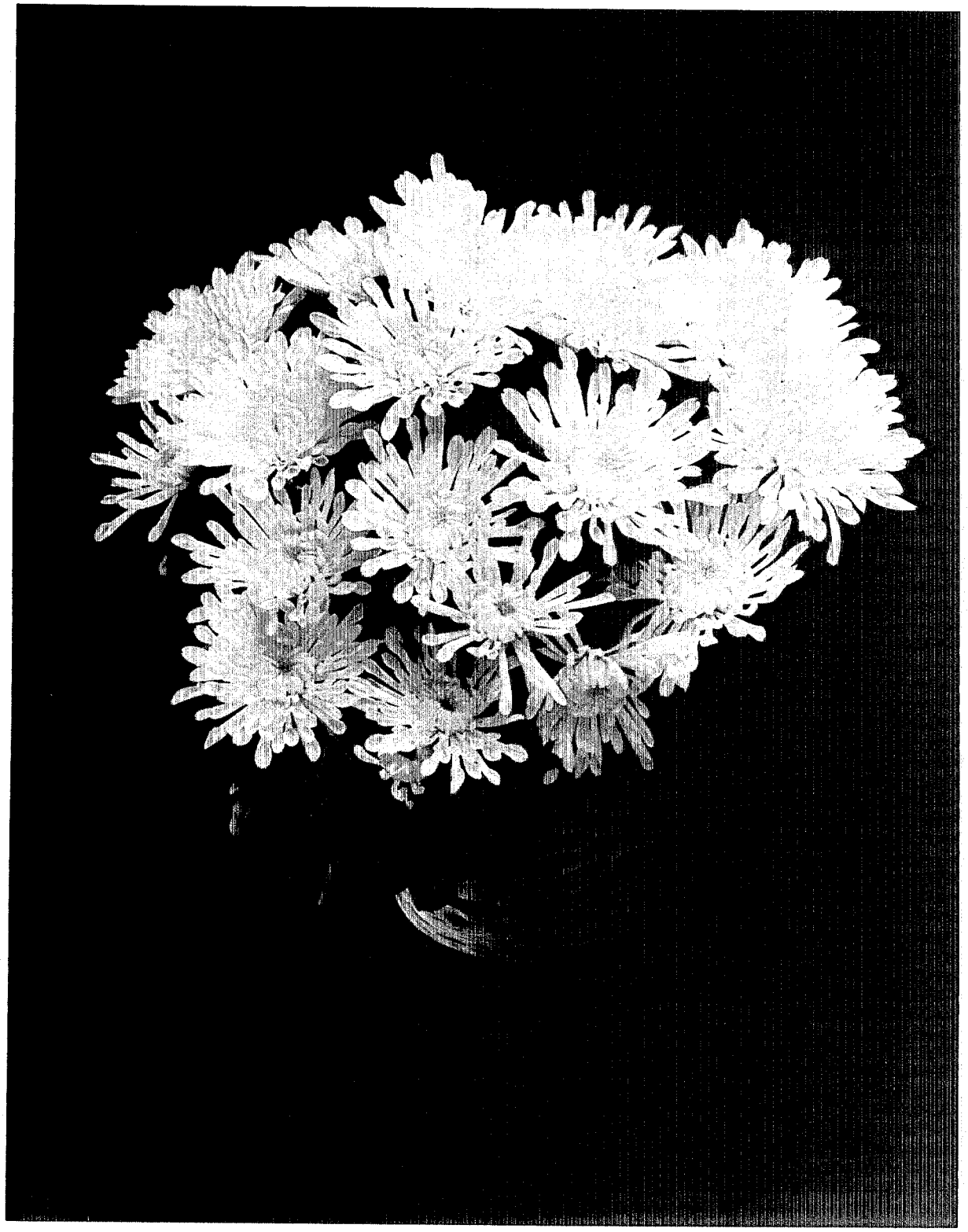

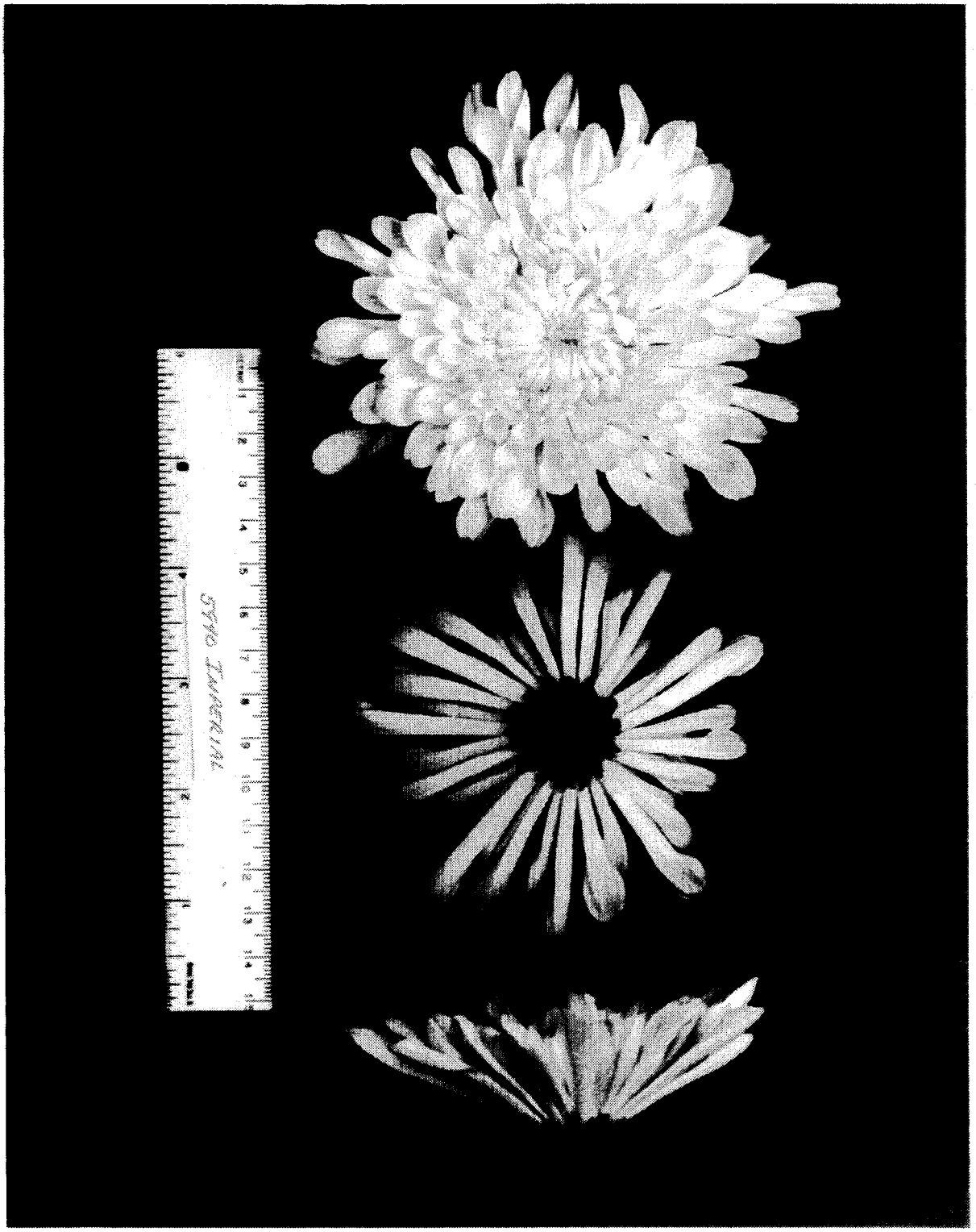
GYPO TANGERINE

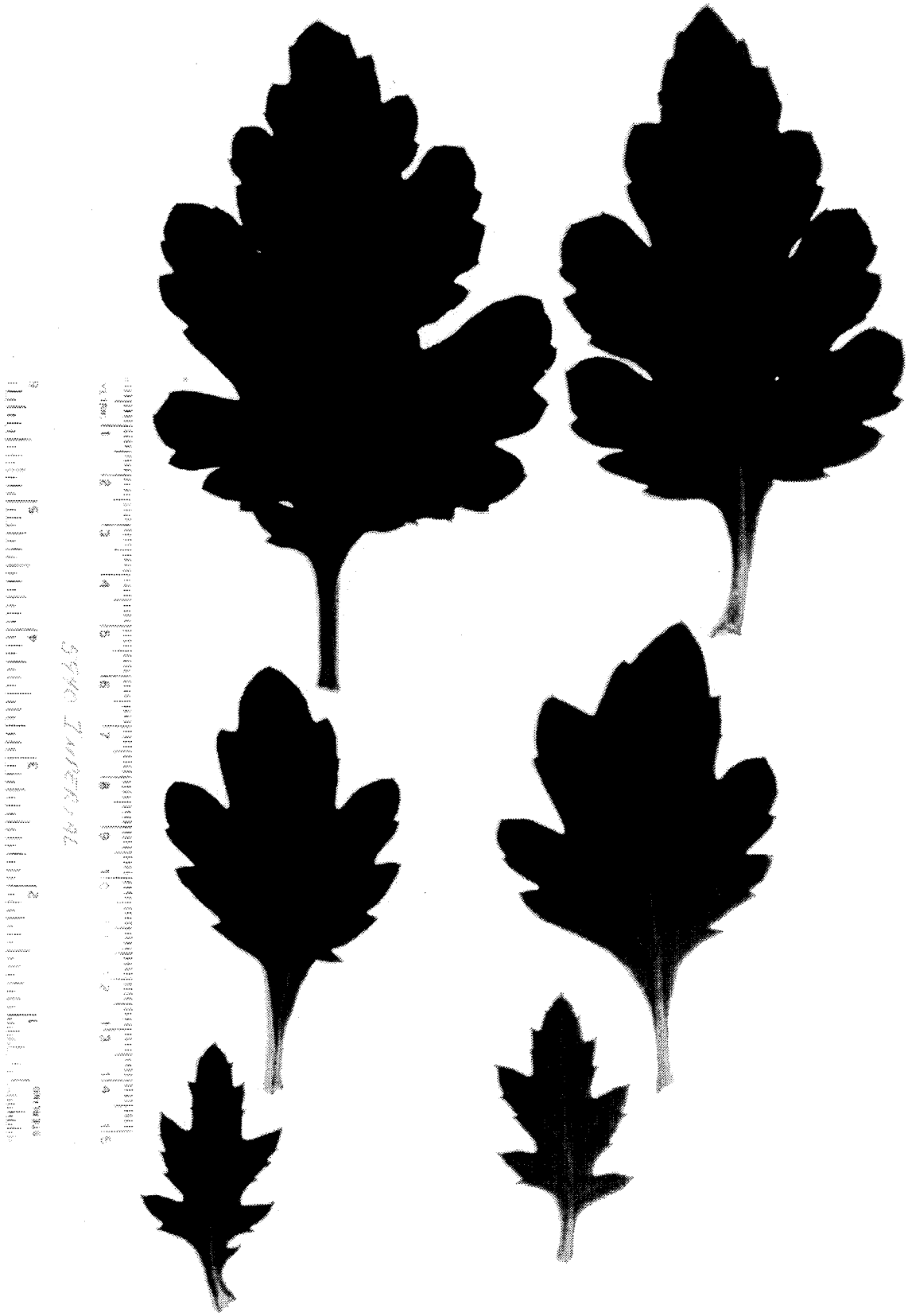
Fig. 3 Inches